United States Patent
Chanduszko

(10) Patent No.: US 12,390,247 B2
(45) Date of Patent: Aug. 19, 2025

(54) THROMBI REMOVAL SYSTEM HAVING A THROMBI REMOVAL CATHETER

(71) Applicant: Bard Peripheral Vascular, Inc., Franklin Lakes, NJ (US)

(72) Inventor: Andrzej J. Chanduszko, Chandler, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 265 days.

(21) Appl. No.: 18/259,172

(22) PCT Filed: Dec. 29, 2020

(86) PCT No.: PCT/US2020/067241
§ 371 (c)(1),
(2) Date: Jun. 23, 2023

(87) PCT Pub. No.: WO2022/146414
PCT Pub. Date: Jul. 7, 2022

(65) Prior Publication Data
US 2024/0050120 A1 Feb. 15, 2024

(51) Int. Cl.
*A61B 17/3207* (2006.01)
*A61M 25/00* (2006.01)
(Continued)

(52) U.S. Cl.
CPC . *A61B 17/320758* (2013.01); *A61M 25/0074* (2013.01); *A61B 2017/00398* (2013.01);
(Continued)

(58) Field of Classification Search
CPC .... A61B 17/320758; A61B 17/320725; A61B 17/32075; A61B 17/320783;
(Continued)

(56) References Cited

U.S. PATENT DOCUMENTS

| 5,084,052 A | 1/1992 | Jacobs |
| 5,273,526 A | 12/1993 | Dance et al. |

(Continued)

FOREIGN PATENT DOCUMENTS

| CN | 209033283 U | 6/2019 |
| CN | 110916768 A | 3/2020 |

(Continued)

OTHER PUBLICATIONS

International Search Report and Written Opinion dated Sep. 8, 2021, in International Application No. PCT/US2020/067421.

*Primary Examiner* — Tuan V Nguyen
(74) *Attorney, Agent, or Firm* — Dinsmore & Shohl LLP

(57) ABSTRACT

A thrombi removal catheter includes a sheath having a distal axial opening at a distal end in fluid communication with a lumen, and a lateral opening that extends through a side wall to the lumen. The lateral opening is proximally spaced from the distal end. An elongate member is disposed in the lumen of the sheath and is configured for longitudinal movement relative to the sheath. The elongate member has a proximal position and a distal position relative to the sheath. When the elongate member is in the proximal position, the distal axial opening of the sheath is closed by a distal blocker element of the elongate member and the lateral opening of the sheath is open, and when the elongate member is in the distal position, the lateral opening of the sheath is closed by the proximal blocker element and the distal axial opening of the sheath is open.

21 Claims, 7 Drawing Sheets

(51) Int. Cl.
*A61B 17/00* (2006.01)
*A61B 17/22* (2006.01)
*A61B 17/32* (2006.01)

(52) U.S. Cl.
CPC ............... *A61B 2017/22079* (2013.01); *A61B 2017/320028* (2013.01); *A61M 2025/0079* (2013.01)

(58) Field of Classification Search
CPC .......... A61B 2017/22079; A61B 2017/00398; A61B 2017/320028; A61M 25/0074; A61M 2025/0079
See application file for complete search history.

(56) References Cited

U.S. PATENT DOCUMENTS

| | | |
|---|---|---|
| 5,417,703 A | 5/1995 | Brown et al. |
| 5,722,985 A | 3/1998 | Pettus |
| 5,873,882 A | 2/1999 | Straub et al. |
| 6,743,197 B1 | 6/2004 | Edwards |
| 7,905,896 B2 | 3/2011 | Straub |
| 8,568,432 B2 | 10/2013 | Straub |
| 9,566,087 B2 | 2/2017 | Bierman et al. |
| 10,426,498 B1 | 10/2019 | Baxter et al. |
| 2003/0125639 A1 | 7/2003 | Fisher et al. |
| 2009/0270808 A1* | 10/2009 | Mas ....................... A61B 17/22 604/119 |
| 2017/0027600 A1 | 2/2017 | Mcdonald |

FOREIGN PATENT DOCUMENTS

| | | |
|---|---|---|
| EP | 1901666 A2 | 3/2008 |
| EP | 2698119 A1 | 2/2014 |
| EP | 3698740 A1 | 8/2020 |

* cited by examiner

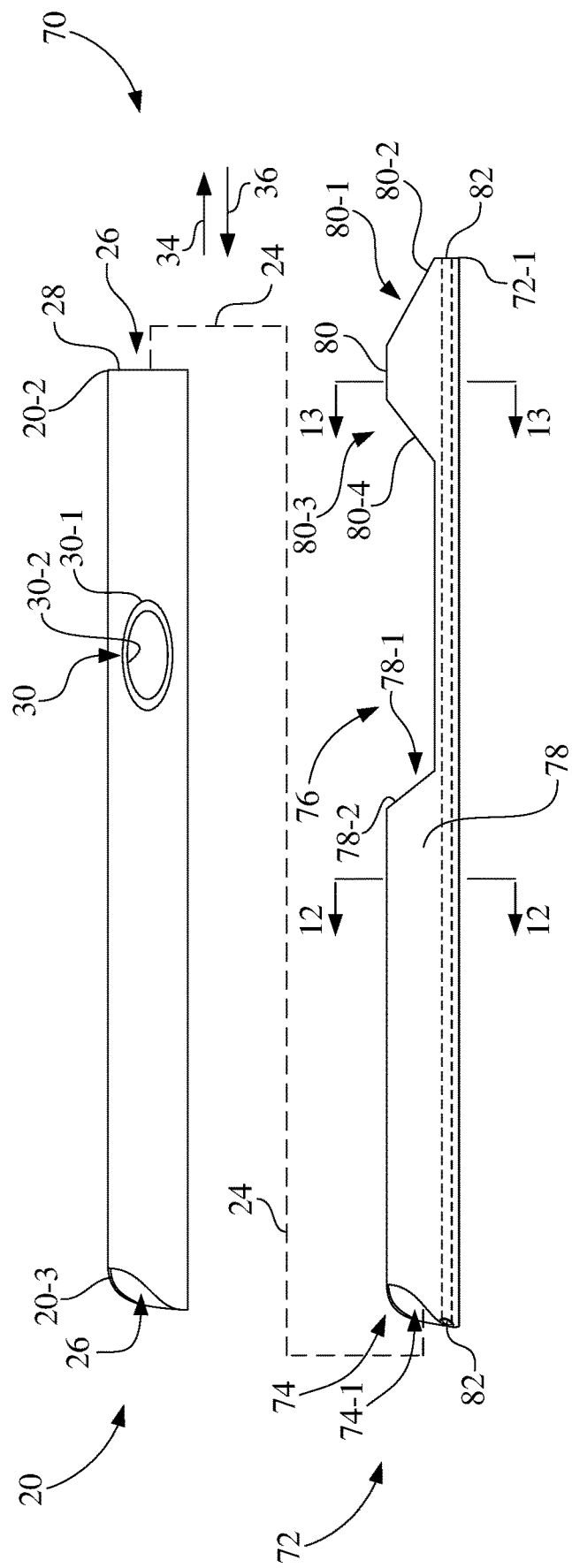
Fig. 11
Fig. 12
Fig. 13

THROMBI REMOVAL SYSTEM HAVING A THROMBI REMOVAL CATHETER

CROSS-REFERENCE TO RELATED APPLICATIONS

This application is a U.S. National Phase of International Application No. PCT/US2020/067241, entitled "Thrombi Removal System Having a Thrombi Removal Catheter" and filed Dec. 29, 2020, which is incorporated herein by reference in its entirety.

TECHNICAL FIELD

The present invention relates to thrombus removal, and, more particularly, to a thrombi removal system having a thrombi removal catheter.

BACKGROUND ART

Thrombosis is a condition wherein a blood clot, known as a thrombus, is formed within a blood vessel, thus obstructing the normal blood flow through the blood vessel. Interventional medical devices, such as catheters, may be used to help breakup and/or remove the thrombus from the blood vessel using static continuous vacuum pressure. However, it has been observed that when static continuous vacuum is applied to a more robust blood clot, the blood clot tends to attach to the tip of the catheter without breaking, hence interrupting the aspiration through the catheter.

What is needed in the art is a thrombi removal system having a thrombi removal catheter which can break up robust blood clots more effectively.

SUMMARY OF INVENTION

The present invention provides a thrombi removal system having a thrombi removal catheter configured to facilitate intermittent and redirected application of vacuum, e.g., to a blood clot in a blood vessel, and which may provide a mechanical component to aid in clot fragmentation.

The invention, in one form, is directed to a thrombi removal catheter for use in a thrombi removal system. The thrombi removal catheter includes an elongate sheath having a proximal end, a distal end, a side wall that defines a lumen that extends from the proximal end to the distal end, a distal axial opening at the distal end in fluid communication with the lumen, and at least one lateral opening that extends through the side wall to the lumen. The at least one lateral opening is proximally spaced from the distal end. An elongate member is disposed in the lumen of the elongate sheath. The elongate member is configured for longitudinal movement relative to the elongate sheath. The elongate member has a proximal position and a distal position relative to a position of the elongate sheath. The elongate member has a proximal blocker element and a distal blocker element that is longitudinally spaced from the proximal blocker element. The proximal blocker element has a longitudinal passage. The thrombi removal catheter is configured such that: when the elongate member is in the proximal position, the distal axial opening of the elongate sheath is closed by the distal blocker element of the elongate member and the at least one lateral opening of the elongate sheath is open, and when the elongate member is in the distal position, the at least one lateral opening of the elongate sheath is closed by the proximal blocker element and the distal axial opening of the elongate sheath is open.

The invention, in another form, is directed to a thrombi removal system. The thrombi removal system includes the thrombi removal catheter as described herein, a vacuum source, and a driver mechanism. The vacuum source is coupled in fluid communication with the lumen of the elongate sheath. The driver mechanism is coupled to at least one of the elongate member and the elongate sheath. The driver mechanism is configured to longitudinally move the elongate member relative to the elongate sheath by longitudinally moving at least one of the elongate member and the elongate sheath.

An advantage of the present invention is that the device of the present invention provides for more effective removal of thrombi and/or allows a greater portion of the thrombus material to be removed.

Another advantage of the present invention is that the thrombi removal system and thrombi removal catheter facilitate and interrupt vacuum application to the area of the thrombus so as to fatigue the clot material.

Another advantage of the present invention is that, in combination with the intermittent application of vacuum to the thrombus, the thrombi removal catheter may be longitudinally reciprocated to slice and/or fragment the blood clot mechanically as the thrombi removal catheter comes in contact with the blood clot.

Another advantage of the present invention is that the thrombi removal catheter is configured to engage the blood clot at both of the tip portion of the catheter and at a side location (or side locations) of the catheter, so that any remaining thrombus material is less likely to be left behind.

Yet another advantage of the present invention is that the operator is less likely to have to stop the procedure to manually clear the catheter tip to open a clogged aspiration passage.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 11 is another embodiment of a thrombi removal catheter in accordance with an aspect of the present invention, wherein the elongate member of the thrombi removal catheter of FIGS. 1-10 is replaced with an alternative configuration of an elongate member configured from an elongate cannula;

FIG. 12 is a section view of the proximal blocker element taken along line 12-12 of FIG. 11; and FIG. 13 is a section view of the distal blocker element taken along line 13-13 of FIG. 11.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
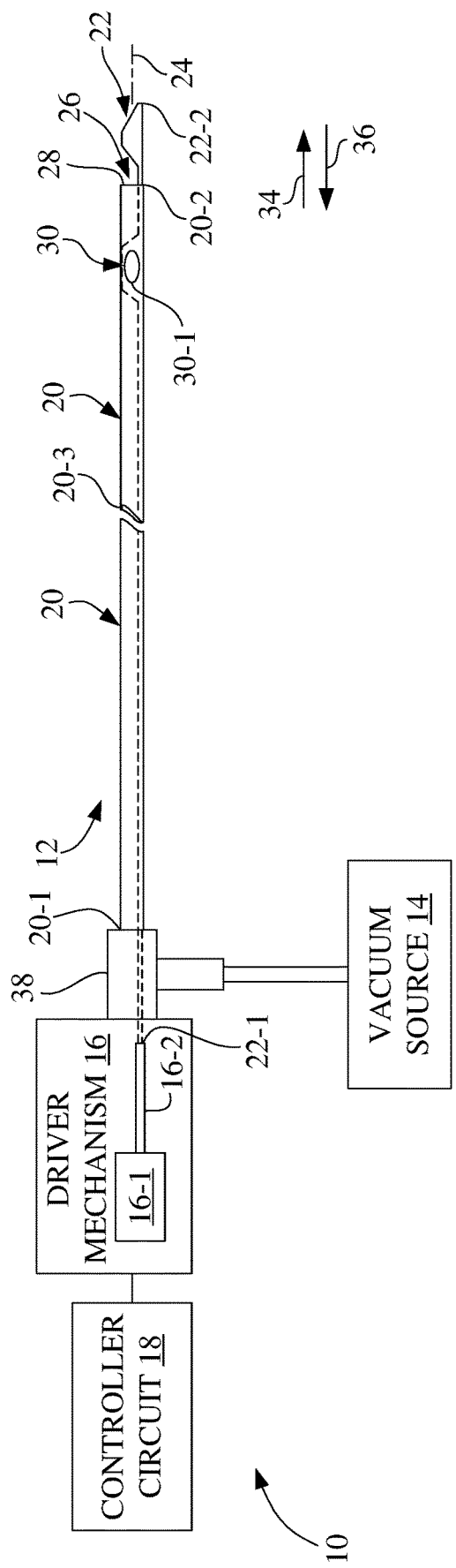
FIG. 1 is a block diagram depicting a thrombi removal system that includes a vacuum source, a driver mechanism, a controller circuit, and a thrombi removal catheter having an inner elongate member disposed in an outer elongate sheath.
Figure 2:
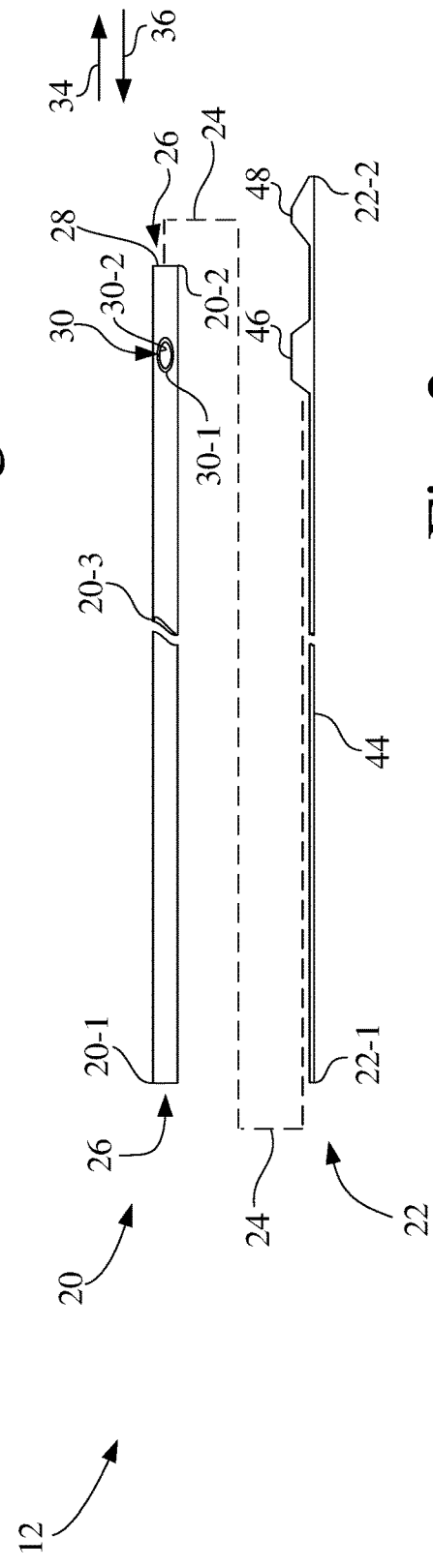
FIG. 2 is an exploded side view of the thrombi removal catheter of FIG. 1, with the elongate member separated from the elongate sheath.

Referring now to the drawings, and more particularly to FIG. 1, there is shown a thrombi removal system 10 that includes a thrombi removal catheter 12, a vacuum source 14, a driver mechanism 16, and a controller circuit 18.

Referring also to FIGS. 2-6, thrombi removal catheter 12 includes an elongate sheath 20 and an elongate member 22 that is coaxial with elongate sheath 20 along a longitudinal axis 24. In the present embodiment, elongate sheath 20 has a lumen 26 and elongate member 22 is slidably disposed in lumen 26 of elongate sheath 20. Elongate member 22 is configured for longitudinal movement relative to elongate sheath 20. Each of elongate sheath 20 and elongate member 22 is made of flexible material so as to be adaptable to a vasculature along its respective longitudinal length. The flexible material may be plastic or metal. Some examples of suitable plastics include Pebax, polyimide, etc. Some examples of suitable metals include stainless steel, nitinol, etc.

Elongate sheath 20 includes a distal axial opening 28 and at least one lateral opening 30. In the present embodiment, the at least one lateral opening 30 is represented as a plurality of lateral openings in elongate sheath 20, wherein the plurality of lateral openings include two diametrically opposed lateral openings, individually identified as lateral opening 30-1 and lateral opening 30-2. Collectively, lateral opening 30-1 and lateral opening 30-2 may be referenced as lateral openings 30-1, 30-2. However, for convenience, the term "lateral opening 30" will be used to reference structure that includes at least one of lateral opening 30-1 and/or lateral opening 30-2, and does not preclude the inclusion of additional lateral openings, e.g., circumferentially spaced between lateral opening 30-1 and lateral opening 30-2. In the present embodiment, lateral opening 30 may be located in a distal section of elongate sheath 20, e.g., near a distal end of elongate sheath 20.

During a thrombectomy, distal axial opening 28 and lateral opening 30 are alternatingly opened and closed by a reciprocating longitudinal movement of elongate member 22 relative to elongate sheath 20 in a distal direction 34 and a proximal direction 36 along longitudinal axis 24. In one embodiment, the cumulative size, i.e., area of the opening, of lateral opening 30 may be selected, for example, to be equal to the size, i.e., area of the opening, of distal axial opening 28. However, alternatively, the cumulative size, i.e., area of the opening, of lateral opening 30 may be selected, for example, to be different from the size, i.e., area of the opening, of distal axial opening 28, so that the flow velocities through lateral opening 30 and through distal axial opening 28 are different. The structure and operation of thrombi removal catheter 12 will be discussed in further detail below.

Vacuum source 14, e.g., a local vacuum pump, is coupled in fluid communication with lumen 26 of elongate sheath 20 of thrombi removal catheter 12 via a connection manifold 38. Connection manifold 38 is configured with openings, passages, and seals to facilitate the interface of vacuum source 14, and driver mechanism 16, with thrombi removal catheter 12. Vacuum source 14 may be controlled by control instructions executed by controller circuit 18, or alternatively, may be a simple ON/OFF switch to operate a vacuum pump, e.g., to selectively supply electrical power to an electrical vacuum pump.

Driver mechanism 16 is drivably coupled to thrombi removal catheter 12 to facilitate the longitudinal movement of elongate member 22 relative to elongate sheath 20 by a longitudinal movement of at least one of elongate member 22 and elongate sheath 20. For example, driver mechanism 16 may be coupled to at least one of elongate member 22 and elongate sheath 20, wherein driver mechanism 16 is configured to longitudinally move elongate member 22 relative to elongate sheath 20 by longitudinally moving at least one of elongate member 22 and elongate sheath 20. In the present, driver mechanism 16 is drivably connected to elongate member 22 so as to longitudinally move elongate member 22 while elongate sheath 20 is not longitudinally driven. Alternatively, for example, driver mechanism 16 may be drivably connected to elongate sheath 20 so as to longitudinally move elongate sheath 20 while elongate member 22 is not longitudinally driven.

In accordance with an aspect of the present invention, driver mechanism 16 is configured to longitudinally move elongate member 22 relative to elongate sheath 20 in a longitudinal reciprocation manner. Driver mechanism 16 may be, for example, a motive power source 16-1 drivably coupled to a linear drive member 16-2, wherein the linear drive member 16-2 is mechanically coupled to one of elongate member 22 and elongate sheath 20. In one example, the motive power source 16-1 is a rotary motor and the linear drive member 16-2 is a rotational-to-linear translation (e.g., pinion/rack) gear assembly. In another example, the motive power source 16-1 is a linear motor and the linear drive member 16-2 is a magnetic linear translator core member. In another example, the motive power source 16-1 is a solenoid and the linear drive member 16-2 is a ferrous linear translator core member. In the case that the driver mechanism 16 is an electrical power source, the motive power source 16-1 supplies electrical energy. In the case that the driver mechanism 16 is a pneumatic power source, the motive power source 16-1 supplies fluid energy (e.g., air pressure, positive and/or negative).

Controller circuit 18 is communicatively coupled to driver mechanism 16. Controller circuit 18 may include a user interface, e.g., in the form of operator buttons and/or a touch screen display. Controller circuit 18 is configured to operate driver mechanism 16 to alternatingly position elongate member 22 in a proximal position 40 (see FIG. 3; i.e., a retracted position) and a distal position 42 (see FIG. 4; i.e., an extended position) relative to elongate sheath 20. Controller circuit 18 may be a commercially available microcontroller, or alternatively, may be formed as one or more Application Specific Integrated Circuits (ASIC). In the present embodiment, controller circuit 18 includes one or more programmable microprocessors and associated circuitry, such as an input/output interface, clock, buffers, non-transitory electronic memory, etc. Such non-transitory electronic memory may include volatile memory circuits, such as random access memory (RAM), and non-volatile memory circuits, such as read only memory (ROM), electronically erasable programmable ROM (EEPROM), NOR flash memory, NAND flash memory, etc.

Controller circuit 18 is configured via software and/or firmware to execute program instructions to perform functions, such as effecting a longitudinal reciprocation of elongate member 22 relative to elongate sheath 20 of thrombi removal catheter 12. For example, controller circuit 18 may be configured, e.g., via execution of program instructions, to operate driver mechanism 16 to alternate the positioning of elongate member 22 relative to elongate sheath 20 during reciprocation at a predetermined time interval. The predetermined time interval may be, for example, in a range of 0.05 and 2.5 seconds. Also, a full cycle of reciprocating movement of elongate member 22 relative to elongate sheath 20 may be, for example, a time period in a range of 0.1 seconds to 5 seconds.

Referring to FIGS. 1-8, elongate sheath 20 has a proximal end 20-1, a distal end 20-2, and a side wall 20-3 that defines lumen 26. In the present embodiment, each of lumen 26 and side wall 20-3 extends from proximal end 20-1 to distal end 20-2. In the present embodiment, proximal end 20-1 is connected to connection manifold 38 (see also FIG. 1). Distal axial opening 28 is located at distal end 20-2 and is in fluid communication with lumen 26.

In the present embodiment, with reference to FIGS. 2-5, each of the lateral openings 30-1, 30-2 radially extends through side wall 20-3 to lumen 26. Each of the lateral openings 30-1, 30-2 is proximally spaced from distal end 20-2 of elongate sheath 20. By way of example, and not by limitation, the spacing between distal end 20-2 of elongate sheath 20 and lateral opening 30 may be in a range of 0.5 to 1.5 centimeters.

Figure 3:
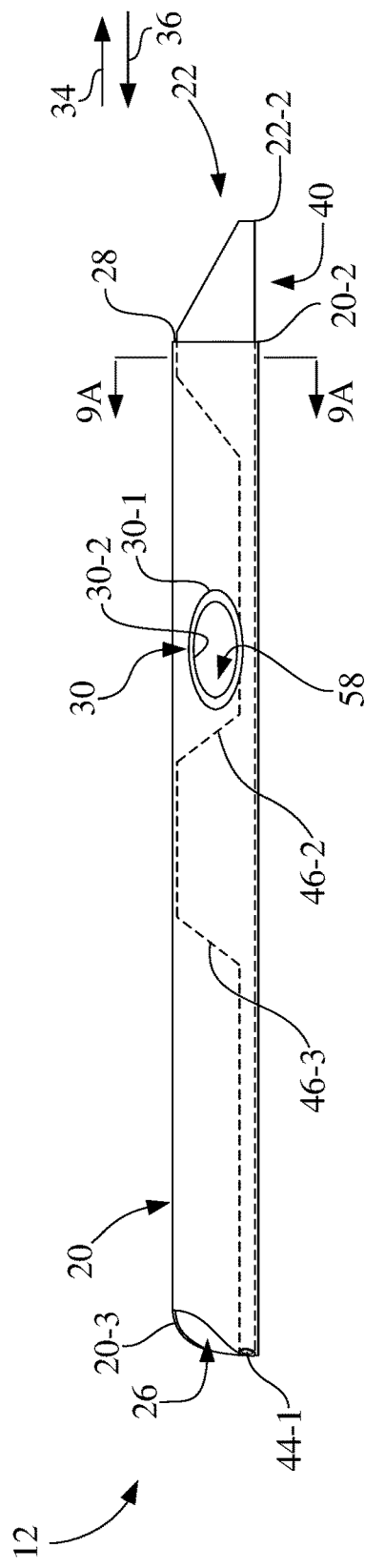
FIG. 3 is an enlarged side view of a distal portion of the thrombi removal catheter of FIGS. 1 and 2, wherein the elongate member is positioned in a proximal position relative to the elongate sheath.
Figure 4:
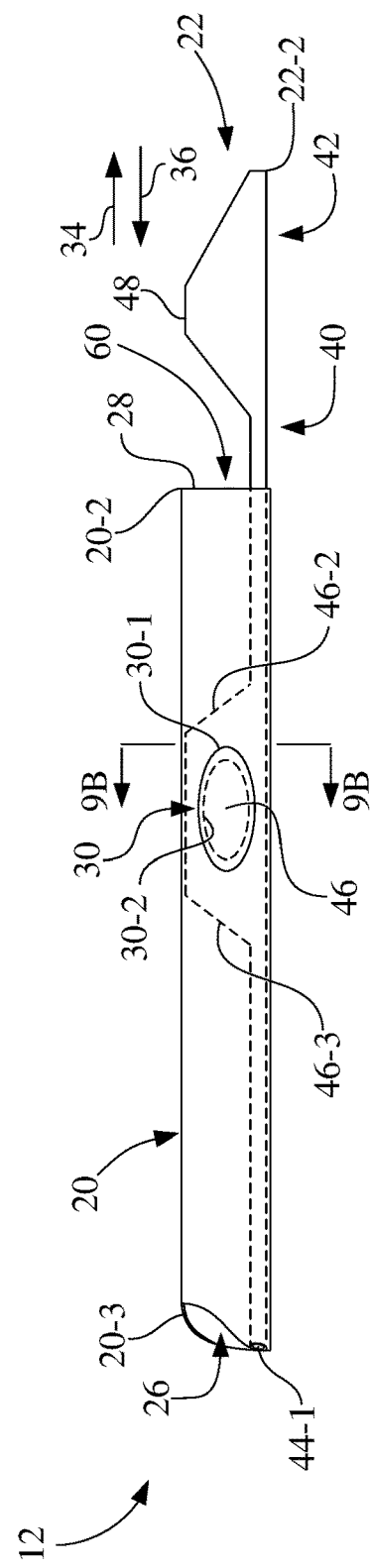
FIG. 4 is an enlarged side view of a distal portion of the thrombi removal catheter of FIGS. 1 and 2, wherein the elongate member is positioned in a distal position relative to the elongate sheath.

In the present embodiment, elongate member 22 is disposed in lumen 26 of elongate sheath 20. Elongate member 22 is configured, e.g., in size and in shape, for longitudinal movement relative to elongate sheath 20. Referring to FIGS. 3 and 4, elongate member 22 has a proximal position 40 and a distal position 42 relative to a position of elongate sheath 20.

Figure 5:
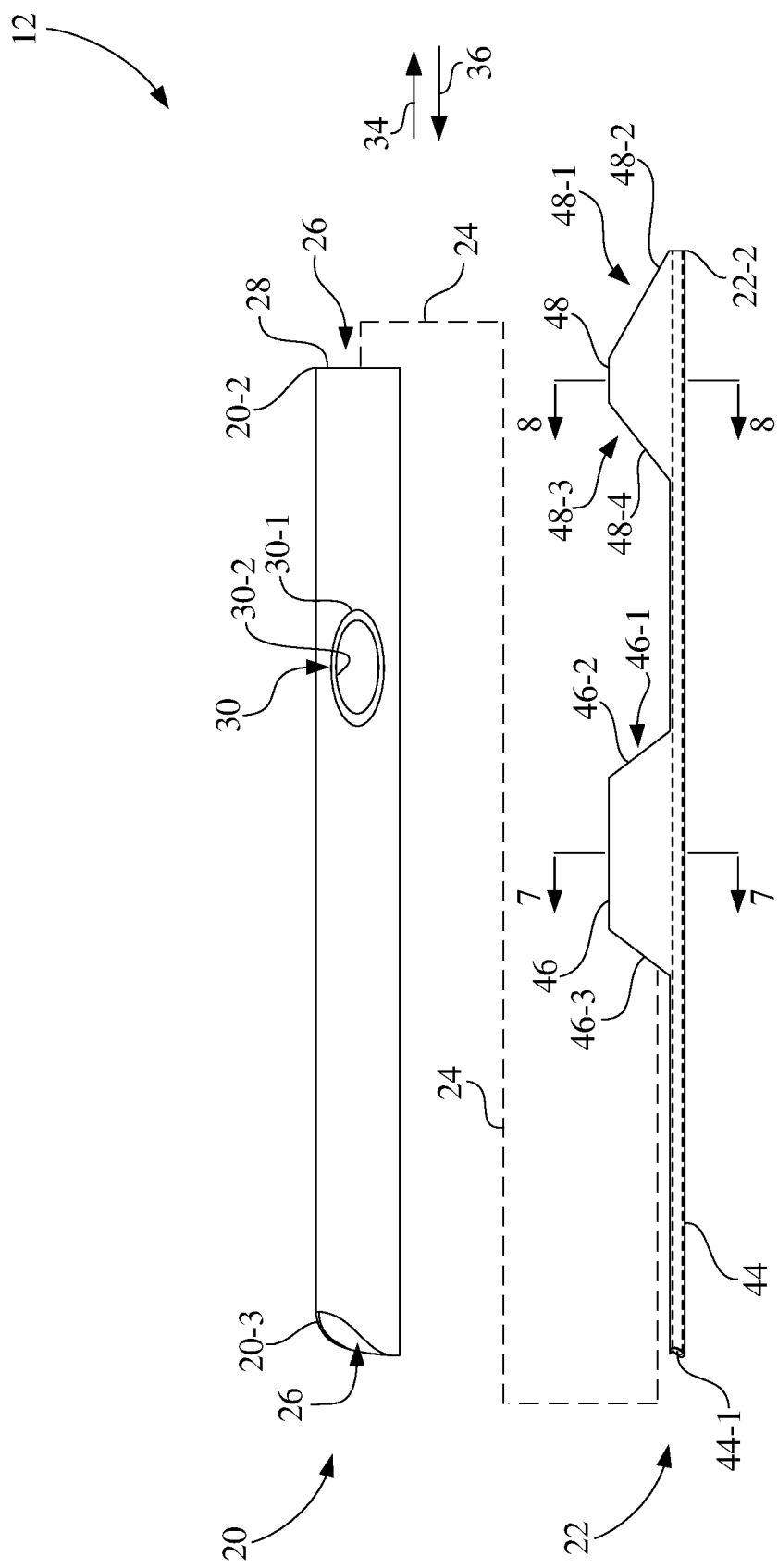
FIG. 5 is an enlargement of a distal portion of the exploded side view of the thrombi removal catheter as depicted in FIG. 2, wherein the elongate member includes an elongate element, a proximal blocker element, and a distal blocker element.
Figure 6:
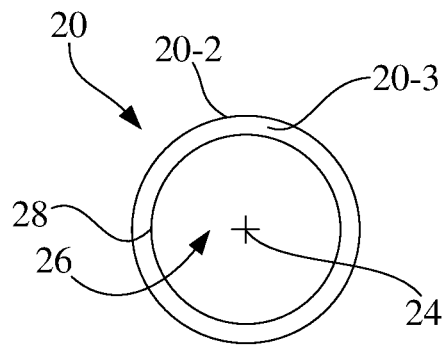
FIG. 6 is an end view of the elongate sheath of FIGS. 1-5.

Referring to FIGS. 3-5, elongate member 22 has a proximal end 22-1 and a distal end 22-2. In the present embodiment, proximal end 22-1 of elongate member 22 is mechanically coupled, e.g., via a threaded coupling, snap coupling, crimping, or weld, to linear drive member 16-2 of driver mechanism 16 (see also FIG. 1). Elongate member 22 further includes an elongate element 44, a proximal blocker element 46, and a distal blocker element 48 that are arranged between proximal end 22-1 and distal end 22-2 of elongate member 22. In the present embodiment, elongate element 44 extends from proximal end 22-1 and distal end 22-2 of elongate member 22. In the present embodiment, proximal blocker element 46 may be located in a distal section of elongate member 22, e.g., near distal end 22-2 of elongate member 22 proximal to distal blocker element 48.

In the present embodiment, elongate element 44 may be configured as an elongate cannula, i.e., a tube, having a guidewire lumen 44-1. Guidewire lumen 44-1 is configured, e.g., in size and shape, to receive a guidewire during a thrombectomy so as to guide thrombi removal catheter 12 to the blood clot.

Distal blocker element 48 is located proximate distal end 22-2 of elongate member 22. In the present embodiment, distal blocker element 48 extends proximally from distal end 22-2 of elongate member 22. Distal blocker element 48 is longitudinally spaced from proximal blocker element 46. Distal blocker element 48 is connected to elongate element 44, such as for example, by weld, solder, or an adhesive, or may be formed integral with elongate element 44 via molding.

Proximal blocker element 46 is located proximal to distal blocker element 48. Proximal blocker element 46 is connected to elongate element 44, such as for example, by weld, solder, or an adhesive, or may be formed integral with elongate element 44 via molding. By way of example, and not by limitation, the spacing between proximal blocker element 46 and distal blocker element 48 may be in a range of 0.5 to 1.5 centimeters.

Figure 7:
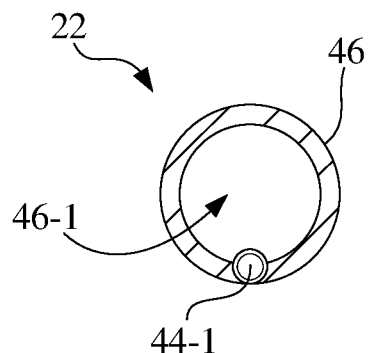
FIG. 7 is an enlarged view of the proximal blocker element taken along line 7-7 of FIG. 5.

Referring also to FIG. 7, proximal blocker element 46 has a longitudinal passage 46-1. With elongate member 22 disposed in lumen 26 of elongate sheath 20, longitudinal passage 46-1 of proximal blocker element 46 is in fluid communication with lumen 26. Proximal blocker element 46 may be configured, for example, as a cylinder having longitudinal passage 46-1. Referring to FIGS. 3-5, proximal blocker element 46 has a beveled distal end 46-2. Optionally, proximal blocker element 46 may include a beveled proximal end 46-3. In the present embodiment, beveled distal end 46-2 is configured, e.g., in size and in shape, to longitudinally pass across lateral opening 30 (e.g., each lateral opening 30-1, 30-2) of side wall 20-3 of elongate sheath 20 to effect a scissoring cutting action as elongate member 22 longitudinally moves from proximal position 40 to distal position 42.

Figure 8:
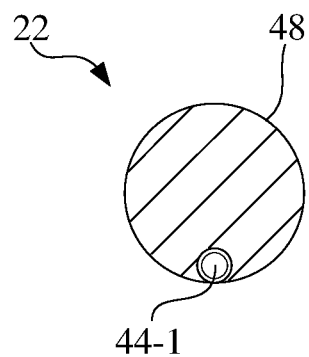
FIG. 8 is an enlarged section view of the distal blocker element taken along line 8-8 of FIG. 5.

Referring also to FIG. 8 in conjunction with FIGS. 3-5, in the present embodiment, distal blocker element 48 may be a solid structure, or at least a radially closed structure, that has a closed distal end 48-1 that defines a tapered tip 48-2, and may have a closed proximal end 48-3 that defines a proximal beveled surface 48-4. Tapered tip 48-2 may be, for example, beveled or pointed. Referring to FIGS. 3-5, proximal beveled surface 48-4 is configured, e.g., in size and in shape, to longitudinally pass into distal axial opening 28 of elongate sheath 20 and across distal end 20-2 of side wall 20-3 of elongate sheath 20 to effect a scissoring cutting action as elongate member 22 longitudinally moves from distal position 42 to proximal position 40.

Figure 9A:
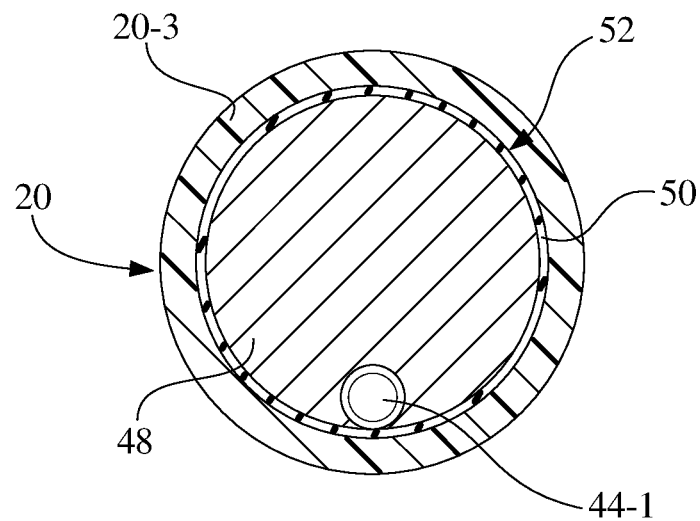
FIG. 9A is a section view of an optional embodiment, associated with line 9A-9A of FIG. 3, wherein an annular seal may be radially interposed between a side wall of the elongate sheath and the distal blocker element of the elongate member.

Referring to FIG. 9A, optionally, a first annular seal 50 may be radially interposed between side wall 20-3 of elongate sheath 20 and distal blocker element 48 of elongate member 22. First annular seal 50 may be in the form of an O-ring, a rubber sleeve, or a rubberized coating. Referring to FIG. 9A in conjunction with FIG. 3, first annular seal 50 is configured, e.g., in thickness and position, to seal an annular region 52 between side wall 20-3 of elongate sheath 20 and distal blocker element 48 when distal blocker element 48 is in proximal position 40.

Figure 9B:
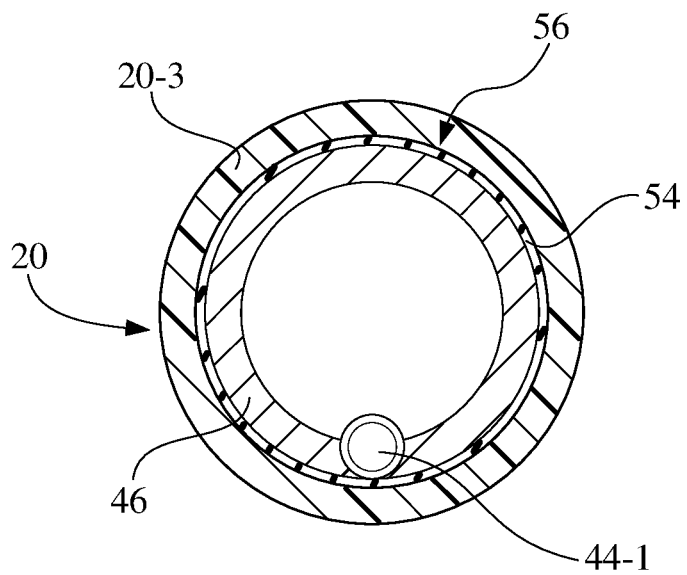
FIG. 9B is a section view of an optional embodiment, associated with line 9B-9B of FIG. 4, wherein an annular seal may be radially interposed between the side wall of the elongate sheath and the proximal blocker element of the elongate member.

Similarly, referring to FIG. 9B, optionally, a second annular seal 54 may be radially interposed between side wall 20-3 of elongate sheath 20 and proximal blocker element 46 of elongate member 22. Second annular seal 54 may be in the form of an O-ring, a rubber sleeve, or a rubberized coating. Referring to FIG. 9B in conjunction with FIG. 4, second annular seal 54 is configured, e.g., in thickness and position, to seal an annular region 56 between side wall 20-3 of elongate sheath 20 and proximal blocker element 46 when proximal blocker element 46 is in distal position 42.

In operation, with reference to FIGS. 3 and 4, when elongate member 22 is in proximal position 40, distal axial opening 28 of elongate sheath 20 is closed by distal blocker element 48 of elongate member 22 and lateral opening 30 (e.g., each lateral opening 30-1, 30-2) of elongate sheath 20 is open. As such, when elongate member 22 is in proximal position 40, a first fluid path 58 is defined through lateral opening 30 (e.g., each of lateral opening 30-1, 30-2) to lumen 26 of elongate sheath 20 to the exclusion of distal axial opening 28. First fluid path 58 also extends through longitudinal passage 46-1 of proximal blocker element 46 to facilitate fluid communication of lateral opening 30 (e.g., each lateral opening 30-1, 30-2) of elongate sheath 20 with vacuum source 14. As such, when elongate member 22 is in proximal position 40, aspiration is effected by vacuum source 14 at lateral opening 30 to the exclusion of distal axial opening 28.

Conversely, when elongate member 22 is in distal position 42, lateral opening 30 (e.g., each lateral opening 30-1, 30-2) of elongate sheath 20 is closed by proximal blocker element 46 and distal axial opening 28 of elongate sheath 20 is open. As such, when elongate member 22 is in distal position 42, a second fluid path 60 (different from first fluid path 58) is defined through distal axial opening 28 to lumen 26 of elongate sheath 20 to the exclusion of lateral opening 30 (e.g., to the exclusion of each lateral opening 30-1, 30-2). Second fluid path 60 extends through longitudinal passage 46-1 of proximal blocker element 46 to facilitate fluid communication of distal axial opening 28 of elongate sheath 20 with vacuum source 14. As such, when elongate member 22 is in distal position 42, aspiration is effected by vacuum source 14 at distal axial opening 28 to the exclusion of lateral opening 30.

Thus, in accordance with the present embodiment, each of first fluid path 58 and second fluid path 60 extends through longitudinal passage 46-1 of proximal blocker element 46, but the selection as between first fluid path 58 through lateral opening 30 or second fluid path 60 through distal axial opening 28 depends upon the position of elongate member 22 at proximal position 40 or at distal position 42.

In one implementation of the present invention, controller circuit 18 executes program instructions to operate driver mechanism 16 so as to alternatingly position elongate member 22 in proximal position 40 (see FIG. 3) and distal position 42 (see FIG. 4) relative to elongate sheath 20. For example, controller circuit 18 may execute program instructions to alternate the positioning of elongate member 22 relative to elongate sheath 20 in proximal position 40 and distal position 42 at a predetermined time interval. As such, vacuum applied to the thrombus alternates between first fluid path 58 through lateral opening 30 (e.g., each lateral opening 30-1, 30-2) of elongate sheath 20, and second fluid path 60 through distal axial opening 28 of elongate sheath 20.

In the present embodiment, for example, the predetermined time interval is in a range of 0.05 and 2.5 seconds. Stated differently, a full cycle of movement of elongate sheath 20 from proximal position 40 to distal position 42, and back to proximal position 40, has a time period in a range of 0.1 seconds to 5 seconds. The number of full cycles may be determined by the user, such as for example, by user observation, or in some implementations, may be a predetermined value stored in controller circuit 18.

Figure 10:
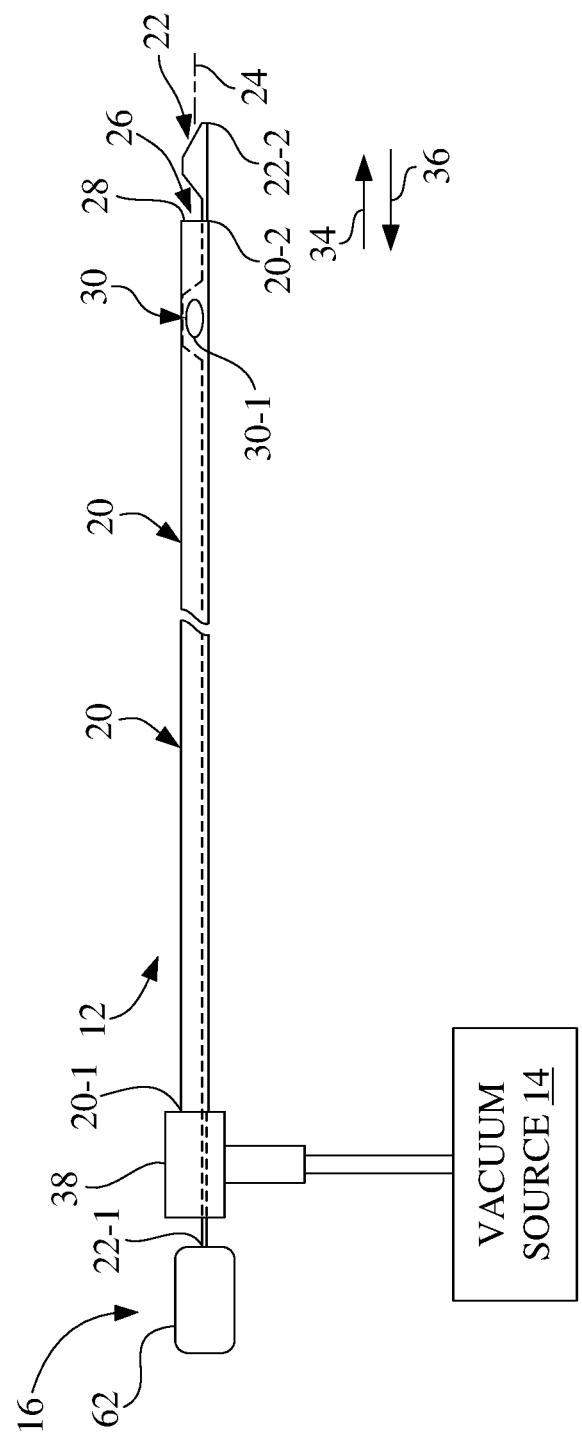
FIG. 10 is a modification of the embodiment of FIG. 1, wherein the controller circuit of FIG. 1 is omitted and the driver mechanism is in the form of a manual handle.

FIG. 10 shows another embodiment of the present invention, wherein driver mechanism 16 is a manual handle 62 that is connected to one of elongate member 22 and elongate sheath 20, so as to alternatingly position elongate member 22 in proximal position 40 (see FIG. 3) and distal position 42 (see FIG. 4) relative to elongate sheath 20. Controller circuit 18 of FIG. 1 may also be removed in the embodiment of FIG. 10, wherein vacuum source 14 is then manually activated, e.g., by an ON/OFF switch.

Referring to FIGS. 11-13, there is shown another embodiment for a thrombi removal catheter 70 in accordance with an aspect of the present invention that may replace thrombi removal catheter 12 of FIG. 1. Thrombi removal catheter 70 includes elongate sheath 20 and an elongate member 72 that is coaxial with elongate sheath 20 along longitudinal axis 24. Thrombi removal catheter 70 differs from thrombi removal catheter 12 in that elongate member 22 is replaced with elongate member 72. As such, the function and operation of thrombi removal catheter 70 is identical to that of thrombi removal catheter 12, discussed above with respect to FIGS. 1-10.

Referring to FIG. 11, elongate member 72 is slidably disposed in lumen 26 of elongate sheath 20. Elongate member 72 is configured for longitudinal movement relative to elongate sheath 20. Each of elongate sheath 20 and elongate member 72 is made of flexible material so as to be adaptable to a vasculature along its respective longitudinal length. The flexible material may be plastic or metal. Some examples of suitable plastics include Pebax, polyimide, etc. Some examples of suitable metals include stainless steel, nitinol, etc.

During a thrombectomy, distal axial opening 28 and the lateral opening 30 (e.g., each lateral opening 30-1, 30-2) are alternatingly opened and closed by a reciprocating longitudinal movement of elongate member 72 relative to elongate sheath 20 in distal direction 34 and proximal direction 36 along longitudinal axis 24.

Referring again to FIGS. 11-13, elongate member 72 is formed as a cannula 74 having a side-section removed to form a notch 76 so as to define a proximal blocker element 78 and a distal blocker element 80, which correspond generally to proximal blocker element 46 and distal blocker element 48 of the embodiment of FIGS. 1-10. Cannula 74 has a lumen 74-1. In the present embodiment, lumen 74-1 of cannula 74 may be coupled in direct fluid communication with vacuum source 14, or may be coupled in indirect fluid communication with vacuum source 14 via lumen 26 of elongate sheath 20.

In the present embodiment, elongate member 72 includes a guidewire lumen 82, e.g., as a separate tube or as a lumen in the side wall of elongate member 72. Guidewire lumen 82 is configured, e.g., in size and shape, to receive a guidewire during a thrombectomy.

Referring to FIGS. 11 and 12, proximal blocker element 78 has a longitudinal passage 78-1 in fluid communication with lumen 74-1 of cannula 74. In the present embodiment, proximal blocker element 78 is configured, for example, as a cylinder having longitudinal passage 78-1. Proximal blocker element 78 has a beveled distal end 78-2. In the present embodiment, beveled distal end 78-2 is configured, e.g., in size and in shape, to longitudinally pass across lateral opening 30 (e.g., each lateral opening 30-1, 30-2) of side wall 20-3 of elongate sheath 20 to effect a scissoring cutting action as elongate member 72 longitudinally moves from proximal position 40 to distal position 42 (see, e.g., FIGS. 3 and 4).

Referring to FIGS. 11 and 13, distal blocker element 80 is longitudinally spaced from proximal blocker element 78, and distal blocker element 80 is located proximate distal end 72-1 of elongate member 72. In the present embodiment, distal blocker element 80 extends proximally from distal end 72-1 of elongate member 72. Distal blocker element 80 includes a closed distal end 80-1 that defines a tapered tip 80-2 and may have a closed proximal end 80-3 that defines a proximal beveled surface 80-4. Distal blocker element 80 may be closed by plugging, e.g., filling, cannula 74 at distal blocker element 80. Proximal beveled surface 80-4 is configured, e.g., in size and in shape, to longitudinally pass into distal axial opening 28 of elongate sheath 20 and across distal end 20-2 of side wall 20-3 of elongate sheath 20 to effect a scissoring cutting action as elongate member 72 longitudinally moves from distal position 42 to proximal position 40 (see, e.g., FIGS. 3 and 4).

The following items also relate to the invention:

In one embodiment, the invention relates to a thrombi removal catheter for use in a thrombi removal system. The thrombi removal catheter may include an elongate sheath having a proximal end, a distal end, a side wall that defines a lumen that extends from the proximal end to the distal end, a distal axial opening at the distal end in fluid communication with the lumen, and at least one lateral opening that extends through the side wall to the lumen. The at least one lateral opening is proximally spaced from the distal end. An elongate member is disposed in the lumen of the elongate sheath. The elongate member is configured for longitudinal movement relative to the elongate sheath. The elongate member has a proximal position and a distal position relative to a position of the elongate sheath. The elongate member has a proximal blocker element and a distal blocker element that is longitudinally spaced from the proximal blocker element. The proximal blocker element has a longitudinal passage. The thrombi removal catheter is configured such that: when the elongate member is in the proximal position, the distal axial opening of the elongate sheath is closed by the distal blocker element of the elongate member and the at least one lateral opening of the elongate sheath is open; and when the elongate member is in the distal position, the at least one lateral opening of the elongate sheath is closed by the proximal blocker element and the distal axial opening of the elongate sheath is open.

In any of the embodiments, the thrombi removal catheter may be configurable such that when the elongate member is in the proximal position, a first fluid path may be defined through the at least one lateral opening to the lumen of the elongate sheath to the exclusion of the distal axial opening, and when the elongate member is in the distal position, a second fluid path may be defined through the distal axial opening to the lumen of the elongate sheath to the exclusion of the at least one lateral opening.

In the embodiment of the preceding paragraph, each of the first fluid path and the second fluid path may extend through the longitudinal passage of the proximal blocker element.

In any of the embodiments, the at least one lateral opening may be one of a plurality of side openings in the elongate sheath.

In the embodiment of the preceding paragraph, the plurality of side openings may include two diametrically opposed lateral openings.

In any of the embodiments, the proximal blocker element may be a cylinder.

In any of the embodiments, the proximal blocker element may have a beveled distal end configured to longitudinally pass across each of the at least one lateral opening of the side wall of the elongate sheath to effect a scissoring cutting action as the elongate member longitudinally moves from the proximal position to the distal position.

In any of the embodiments, the distal blocker element may have a closed distal end that defines a pointed tip and a closed proximal end that defines a proximal beveled surface, wherein the proximal beveled surface may be configured to longitudinally pass across the distal end of the side wall of the elongate sheath to effect a scissoring cutting action as the elongate member longitudinally moves from the distal position to the proximal position.

In any of the embodiments, optionally, the elongate member may include an elongate cannula that may have a guidewire lumen. The elongate cannula may have a first end and a second end. The distal blocker element may be located proximate the second end of the elongate cannula and the distal blocker element may be connected to the elongate cannula. The proximal blocker element may be located proximal to the distal blocker element and the proximal blocker element may be connected to the elongate cannula.

In any of the embodiments, optionally, a first annular seal may be radially interposed between the side wall of the elongate sheath and the distal blocker element. The first annular seal may be configured to seal an annular region between the side wall of the elongate sheath and the distal blocker element when the distal blocker element is in the proximal position. A second annular seal may be radially interposed between the side wall of the elongate sheath and the proximal blocker element. The second annular seal may be configured to seal an annular region between the side wall of the elongate sheath and the proximal blocker element when the proximal blocker element is in the distal position.

In any of the embodiments, each of the elongate sheath and the elongate member may be made of flexible material so as to be adaptable to a vasculature along its respective longitudinal length.

In another embodiment, the invention relates to a thrombi removal system that may include the thrombi removal catheter according to any of previous embodiments. The thrombi removal system may also include a vacuum source coupled in fluid communication with the lumen of the elongate sheath. A driver mechanism may be coupled to at least one of the elongate member and the elongate sheath. The driver mechanism may be configured to longitudinally move the elongate member relative to the elongate sheath by longitudinally moving at least one of the elongate member and the elongate sheath.

In any embodiment of the thrombi removal system, the driver mechanism may be configured to longitudinally move the elongate member relative to the elongate sheath in a longitudinal reciprocation manner.

In the embodiment of the preceding paragraph, the driver mechanism may be a motive power source drivably coupled to a linear drive member. The linear drive member may be mechanically coupled to one of the elongate member and the elongate sheath.

In the embodiment of the preceding paragraph, the motive power source may be one of a rotary motor, a linear motor, and solenoid. The motive power source may be configured to be powered by one of electrical energy and fluid energy.

In any embodiment having a linear drive member, the linear drive member may be one of a rotational-to-linear gear assembly and a linear translator core member.

In any embodiment of the thrombi removal system, a controller circuit may be communicatively coupled to the driver mechanism. The controller circuit may be configured to operate the driver mechanism to alternatingly position the elongate member in the proximal position and the distal position relative to the elongate sheath.

In any embodiment having a controller circuit, the controller circuit may be configured to operate the driver mechanism to alternate the positioning of the elongate member relative to the elongate sheath in the proximal position and the distal position at a predetermined time interval.

In the embodiment of the preceding paragraph, the predetermined time interval may be in a range of 0.05 and 2.5 seconds.

In any embodiment of the thrombi removal system, the thrombi removal system may be configured (configurable) such that a full cycle of movement of the elongate member relative to the elongate sheath from the proximal position to the distal position, and back to the proximal position, may have a time period in a range of 0.1 seconds to 5 seconds.

In another embodiment of the thrombi removal system, the driver mechanism may be a manual handle connected to one of the elongate member and the elongate sheath.

As used herein, the term "near" and other words of degree are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

Also, as used herein, the term "coupled", and its derivatives, is intended to embrace any operationally functional connection, i.e., a direct connection or an indirect connection.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A thrombi removal catheter for use in a thrombi removal system, comprising:
    an elongate sheath having a proximal end, a distal end, a side wall that defines a lumen that extends from the proximal end to the distal end, a distal axial opening at the distal end in fluid communication with the lumen, and at least one lateral opening that extends through the side wall to the lumen, the at least one lateral opening being proximally spaced from the distal end;
    an elongate member disposed in the lumen of the elongate sheath, the elongate member configured for longitudinal movement relative to the elongate sheath, the elongate member having a proximal position and a distal position relative to a position of the elongate sheath, the elongate member having a proximal blocker element and a distal blocker element that is longitudinally spaced from the proximal blocker element, the proximal blocker element having a longitudinal passage;
    the thrombi removal catheter configured such that:
    when the elongate member is in the proximal position, the distal axial opening of the elongate sheath is closed by the distal blocker element of the elongate member and the at least one lateral opening of the elongate sheath is open; and
    when the elongate member is in the distal position, the at least one lateral opening of the elongate sheath is closed by the proximal blocker element and the distal axial opening of the elongate sheath is open.

2. The thrombi removal catheter according to claim 1, wherein when the elongate member is in the proximal position, a first fluid path is defined through the at least one lateral opening to the lumen of the elongate sheath to the exclusion of the distal axial opening, and when the elongate member is in the distal position, a second fluid path is defined through the distal axial opening to the lumen of the elongate sheath to the exclusion of the at least one lateral opening.

3. The thrombi removal catheter according to claim 2, wherein each of the first fluid path and the second fluid path extends through the longitudinal passage of the proximal blocker element.

4. The thrombi removal catheter according to claim 1, wherein the at least one lateral opening is one of a plurality of side openings in the elongate sheath.

5. The thrombi removal catheter according to claim 4, wherein the plurality of side openings includes two diametrically opposed lateral openings.

6. The thrombi removal catheter according to claim 1, wherein the proximal blocker element is a cylinder.

7. The thrombi removal catheter according to claim 1, wherein the proximal blocker element has a beveled distal end configured to longitudinally pass across each of the at least one lateral opening of the side wall of the elongate sheath to effect a scissoring cutting action as the elongate member longitudinally moves from the proximal position to the distal position.

8. The thrombi removal catheter according to claim 1, wherein the distal blocker element has a closed distal end that defines a pointed tip and a closed proximal end that defines a proximal beveled surface, wherein the proximal beveled surface is configured to longitudinally pass across the distal end of the side wall of the elongate sheath to effect a scissoring cutting action as the elongate member longitudinally moves from the distal position to the proximal position.

9. The thrombi removal catheter according to claim 1, wherein the elongate member includes an elongate cannula having a guidewire lumen, the elongate cannula having a first end and a second end,
    the distal blocker element being located proximate the second end of the elongate cannula and the distal blocker element being connected to the elongate cannula,
    the proximal blocker element being located proximal to the distal blocker element and the proximal blocker element being connected to the elongate cannula.

10. The thrombi removal catheter according to claim 1, comprising:
    a first annular seal radially interposed between the side wall of the elongate sheath and the distal blocker element, the first annular seal configured to seal an annular region between the side wall of the elongate sheath and the distal blocker element when the distal blocker element is in the proximal position; and a second annular seal radially interposed between the side wall of the elongate sheath and the proximal blocker element, the second annular seal configured to seal an annular region between the side wall of the elongate sheath and the proximal blocker element when the proximal blocker element is in the distal position.

11. The thrombi removal catheter according to claim 1, wherein each of the elongate sheath and the elongate member is made of flexible material so as to be adaptable to a vasculature along its respective longitudinal length.

12. A thrombi removal system, comprising:
a thrombi removal catheter according to claim 1;
a vacuum source coupled in fluid communication with the lumen of the elongate sheath; and
a driver mechanism coupled to at least one of the elongate member and the elongate sheath, the driver mechanism configured to longitudinally move the elongate member relative to the elongate sheath by longitudinally moving at least one of the elongate member and the elongate sheath.

13. The thrombi removal system according to claim 12, wherein the driver mechanism is configured to longitudinally move the elongate member relative to the elongate sheath in a longitudinal reciprocation manner.

14. The thrombi removal system according to claim 13, wherein the driver mechanism is a motive power source drivably coupled to a linear drive member, the linear drive member being mechanically coupled to one of the elongate member and the elongate sheath.

15. The thrombi removal system according to claim 14, wherein the motive power source is one of a rotary motor, a linear motor, and solenoid, the motive power source being configured to be powered by one of electrical energy and fluid energy.

16. The thrombi removal system according to claim 14, wherein the linear drive member is one of a rotational-to-linear gear assembly and a linear translator core member.

17. The thrombi removal system according to claim 12, comprising a controller circuit communicatively coupled to the driver mechanism, the controller circuit configured to operate the driver mechanism to alternatingly position the elongate member in the proximal position and the distal position relative to the elongate sheath.

18. The thrombi removal system according to claim 17, wherein the controller circuit is configured to operate the driver mechanism to alternate the positioning of the elongate member relative to the elongate sheath in the proximal position and the distal position at a predetermined time interval.

19. The thrombi removal system according to claim 18, wherein the predetermined time interval is in a range of 0.05 and 2.5 seconds.

20. The thrombi removal system according to claim 12, wherein a full cycle of movement of the elongate member relative to the elongate sheath from the proximal position to the distal position, and back to the proximal position, has a time period in a range of 0.1 seconds to 5 seconds.

21. The thrombi removal system according to claim 12, wherein the driver mechanism is a manual handle connected to one of the elongate member and the elongate sheath.

* * * * *